(12) United States Patent
Brown et al.

(10) Patent No.: US 11,607,269 B2
(45) Date of Patent: *Mar. 21, 2023

(54) STONE SENSE WITH FIBER EROSION PROTECTION AND CAMERA SATURATION PREVENTION, AND/OR ABSENCE-DETECTION SAFETY INTERLOCK

(71) Applicant: Joe Denton Brown, Panama City Beach, FL (US)

(72) Inventors: Joe D. Brown, Panama City Beach, FL (US); Daniel Malphurs, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 16 days.

This patent is subject to a terminal disclaimer.

(21) Appl. No.: 17/400,380

(22) Filed: Aug. 12, 2021

(65) Prior Publication Data

US 2021/0369347 A1 Dec. 2, 2021

Related U.S. Application Data

(63) Continuation of application No. 15/992,609, filed on May 30, 2018, now Pat. No. 11,109,911.
(Continued)

(51) Int. Cl.
*A61B 18/22* (2006.01)
*A61B 18/20* (2006.01)

(52) U.S. Cl.
CPC ...... *A61B 18/22* (2013.01); *A61B 2018/2075* (2013.01); *A61B 2018/2272* (2013.01); *A61B 2018/22853* (2017.05)

(58) Field of Classification Search
CPC .......... A61B 18/22; A61B 2018/22853; A61B 2018/2075; A61B 2018/2272
See application file for complete search history.

(56) References Cited

U.S. PATENT DOCUMENTS

| 6,626,900 B1 * | 9/2003 | Sinofsky | A61B 18/245 606/7 |
| 11,109,911 B2 * | 9/2021 | Brown | A61B 18/22 |

(Continued)

FOREIGN PATENT DOCUMENTS

| JP | H 10200175 A | 7/1998 |
| WO | PCT/US2017/031091 | 5/2017 |

*Primary Examiner* — Catherine M Voorhees
*Assistant Examiner* — Roland Dinga
(74) *Attorney, Agent, or Firm* — Bacon & Thomas, PLLC

(57) ABSTRACT

A system and method for detecting relative location of a surgical laser fiber tip relative to a surgical laser target during a surgical laser procedure utilizes a spectrophotometer to detect radiation indicative of the relative location. For example, the detected radiation may indicate contact between the fiber tip and a stone being subjected to laser lithotripsy, so as to prompt the surgeon to withdraw the fiber tip from the stone and/or take other action to limit contact-induced erosion of the fiber tip, and to avoid saturation of the endoscope camera resulting from the flash that occurs following contact. In addition, the absence of any detected radiation by the spectrophotometer may be used to indicate that the stone is no longer present, or that the fiber tip is no longer aimed at the stone, prompting the operator to reposition the fiber and/or temporarily cease firing of the laser. The main surgical laser may be a pulsed Holmium laser, which is delivered to the target through the optical fiber together with a pulsed 532 nm aiming beam.

15 Claims, 4 Drawing Sheets

Related U.S. Application Data

(60) Provisional application No. 62/580,509, filed on Nov. 2, 2017, provisional application No. 62/513,791, filed on Jun. 1, 2017.

(56) References Cited

U.S. PATENT DOCUMENTS

| | | |
|---|---|---|
| 2014/0031800 A1 | 1/2014 | Ben Oren |
| 2014/0121458 A1 | 5/2014 | St. George |
| 2014/0276101 A1* | 9/2014 | Asselin ............... A61B 5/4887 600/407 |
| 2015/0230864 A1 | 8/2015 | Xuan |
| 2015/0320433 A1 | 11/2015 | Navve |
| 2016/0262834 A1 | 9/2016 | Chia |

* cited by examiner

STONE SENSE WITH FIBER EROSION PROTECTION AND CAMERA SATURATION PREVENTION, AND/OR ABSENCE-DETECTION SAFETY INTERLOCK This application is a continuation of U.S. patent application Ser. No. 15/992,609, which claims the benefit of provisional U.S. Patent Appl. Ser. Nos. 62/580,509, filed Nov. 2, 2017, and 62/513,791, filed Jun. 1, 2017, each of which is incorporated herein by reference.

BACKGROUND OF THE INVENTION

1. Field of the Invention

The invention relates to the field of laser surgery, and in particular to detection of the relative position of a surgical laser fiber tip and target, such as a stone or other pathological entity or tissue, at which the laser is directed.

The detection of relative position may be used to modulate the laser so that the laser pulses only occur at the most opportune moments, thereby expediting the procedure while also protecting surgical equipment and non-target tissue from extraneous pulses. By minimizing the laser pulses for each procedure, the laser and other equipment, including fibers and endoscopes, will experience less wear and increased longevity. Also, shorter surgical times will increase patient safety by reducing the length time that the patient is sedated.

The target may be a kidney stone being treated by laser lithotripsy, and the detection of relative position may be used to detect, and warn of, contact between the stone and fiber tip so that the fiber tip can be immediately pulled away from the stone, before damage due to erosion and/or an image-saturation flash can occur.

The detection of relative position may also be used to detect that the target is not in the firing path of the laser, to prevent accidental firing of the laser into surgical equipment or tissues other than the target, thereby providing an added safety feature and more efficient treatment due to fewer extraneous pulses. This feature may be used separately from the contact detection feature, including in set-ups where contact between the fiber tip and target is prevented by a ferrule or sleeve that provides a standoff between the end face of the fiber and the target.

2. Description of Related Art

Optical fibers can erode very quickly when making contact with kidney stones while performing laser lithotripsy. As a result, the lithotripsy procedure must be repeated paused while the surgeon restrips and recleaves the fiber in order to remove the eroded tip. This can prolong operative time and jeopardize the safety of the patient.

In addition, contact between the optical fiber and the stone can cause a flash that saturates the image from the endoscope camera, temporarily preventing the surgeon from viewing the treatment site, which can also jeopardize patient safety and prolong operative time.

On the other hand, it is possible to prevent contact between the fiber tip and the stone (or other target) by providing a "SoftTip" or similar ferrule or sleeve that serves as a standoff or set-back to physically prevent contact between the end face of the fiber and the stone, as disclosed in International Patent Appl. No. PCT/US17/39091, filed May 4, 2017, and incorporated herein by reference, which has a common applicant with the present application. In that case, contact may be prevented without the need for contact detection. However, a problem still exists in that the stone might not always be in the path of the laser during the lithotripsy procedure, which can cause retro repulsion of the stone, excess wear on the fiber and laser, and the potential for damage to equipment or tissues other than the stone that are in the direct path of the laser.

SUMMARY OF THE INVENTION

The present invention provides a way to determine the relative position of a fiber tip and a laser target. The invention can therefore be used to reduce erosion and endoscope camera saturation by providing early detection, before the occurrence of significant erosion or a camera-saturating-flash, of contact between the tip of the optical fiber and a stone. The invention can alternatively or additionally be used to detect that the target has moved away from, or is not present in, the path of the laser, and therefore avoid firing of the laser into a tissue other than the target.

The relative fiber tip-to-target detection is accomplished by using a spectrophotometer to detect radiation emissions (or reflections) indicative of the presence of a target at a predetermined position relative to the fiber tip. For example, the spectrophotometer may be used to detect emissions or reflections at a wavelength or wavelengths $\lambda 3$ that occur upon contact between the fiber tip and a stone. Upon detection of contact, an alarm or other indication may be provided so that the fiber can be immediately pulled back away from the tissue, before erosion or a flash occurs. In addition, the delivery of radiation by the fiber can be temporarily stopped or reduced to give the surgeon time to react to the detection and pull back the fiber.

Optionally, failure of the spectrophotometer to detect emissions or reflections from the target may be used as an indication that the stone is no longer present in the path of the laser, in which the delivery of the radiation can be stopped until the fiber position is adjusted and the stone is once again properly positioned relative to the fiber tip. This feature can be used even when contact between the fiber and stone is physically prevented by a standoff such as the "SoftTip" disclosed in International Patent Appl. No. PCT/US17/39091.

DETAILED DESCRIPTION OF THE PREFERRED EMBODIMENTS

Figure 1:
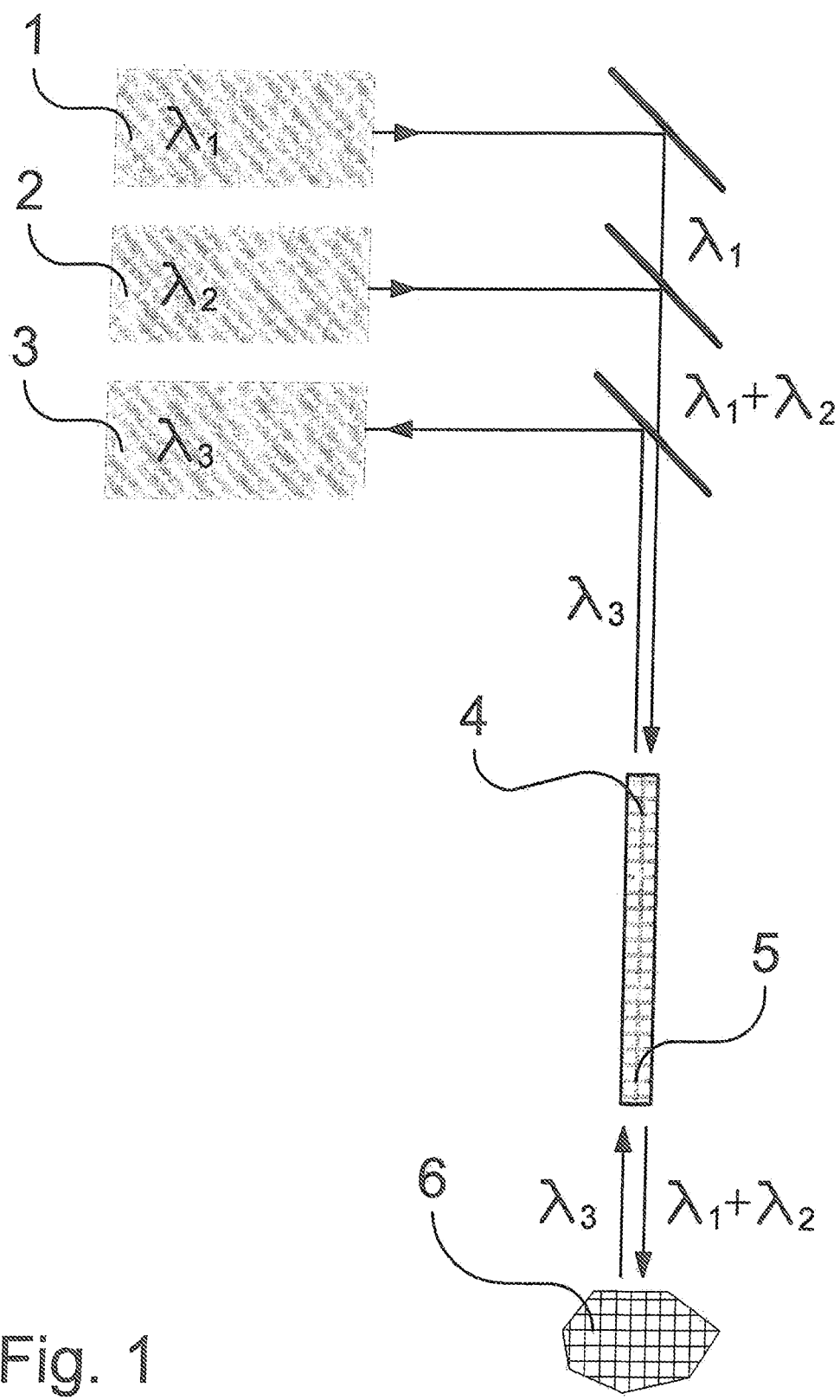
FIG. 1 is a schematic diagram of a contact-sensing system arranged in accordance with the principles of a preferred embodiment of the invention.

As illustrated in FIG. 1, the system of the invention includes a conventional laser delivery apparatus that includes a laser 1 capable of delivering stone vaporizing or destroying pulses during a laser lithotripsy procedure. The system may also include a secondary light source, which could be a laser or LED light source 2 that serves to provide an aiming beam, but which could also be an endoscope light, etc.

The main laser 1 may, by way of example and not limitation, be a Ho:YAG laser that outputs pulses of wavelength $\lambda 1$ at a frequency of 10 Hz. In the illustrative example where a secondary light source 2, which may for example be any pulsed UV-VIS-IR laser, is included to provide an aiming beam. By way of example and not limitation, the aiming beam may have a wavelength $\lambda 2$ of 532 nm (green) that causes the stone to fluoresce at the point of incidence, and that also has a pulse frequency of 10 Hz. The outputs of the of main laser 1 and secondary light source 2 are injected into an optical fiber 4, for delivery through the fiber 5 to the stone 6.

Figure 2:
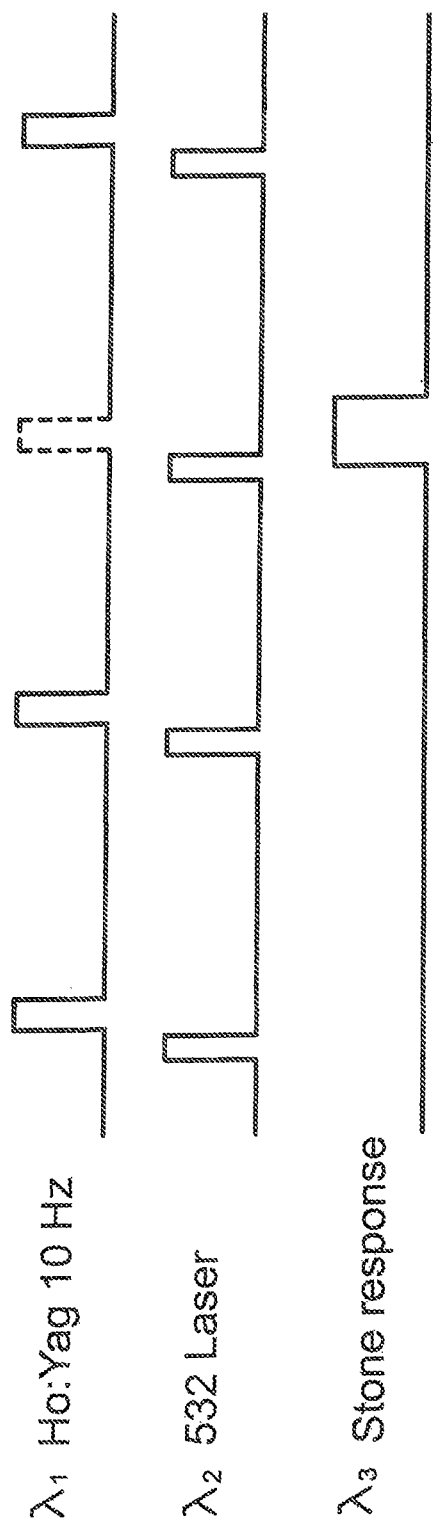
FIG. 2 is a timing diagram for the system of FIG. 1.

The system illustrated in FIG. 1 also includes a spectrophotometer 3 arranged to detect radiation having a wavelength(s) $\lambda 3$ that occurs upon and is indicative of contact between the stone 6 and the fiber tip 5. As shown in FIG. 2, laser 1 and secondary light source 2 deliver respective first and second pulses during a lithotripsy procedure in which the fiber tip 5 is normally positioned adjacent to but not in contact with the stone. However, before the third pulse, the fiber tip 5 contacts the stone 6, causing a responsive radiation emission at wavelength(s) $\lambda 3$, which is detected by the spectrophotometer 3. Alternatively, the secondary light source could come from the endoscope and/or the scope image detection could pick up the radiation of wavelength(s) $\lambda 3$ that occurs upon contact between the fiber tip 5 and the stone 6.

Detection of a threshold level of radiation at wavelength(s) $\lambda 3$ can be used to generate an alarm or contact signal that prompts the surgeon to withdraw the fiber tip from the stone, and/or optionally trigger cut-off, cut-on, or modulation of the main laser 1, before significant erosion and a camera-saturating flash occur. After pull-back of the laser tip 5 from the stone 6, the lithotripsy operation can proceed as normal, as indicated by the fourth main and aiming beam pulses illustrated in FIG. 2.

As an additional feature, some tissues like stones re-emit an optical signature composed of multiple wavelengths when illuminated by the light of wavelength $\lambda 2$, such that the stone composition can be determined with the spectrophotometer 3. As a result, the detected radiation $\lambda 3$ may be comprised of multiple wavelengths and intensities. This information could be useful for diagnostic purposes or help determine laser output parameters.

Alternatively, the failure to detect radiation at a wavelength indicative that the target is present and being irradiated may be used to trigger a warning that the target is not present, or to trigger an automatic shut off or attenuation of the laser. The wavelength indicative that the target is present may be the same wavelength(s) $\lambda 3$ used to indicate contact, but at a level lower than the contact threshold, or the wavelength or wavelengths being monitored for their presence could be different from wavelength(s) $\lambda 3$. Conversely, the laser may also be provided with an active mode that allows the laser to automatically pulse after detecting radiation reflected or emitted by the target when it is in an optimal position.

Figure 3:
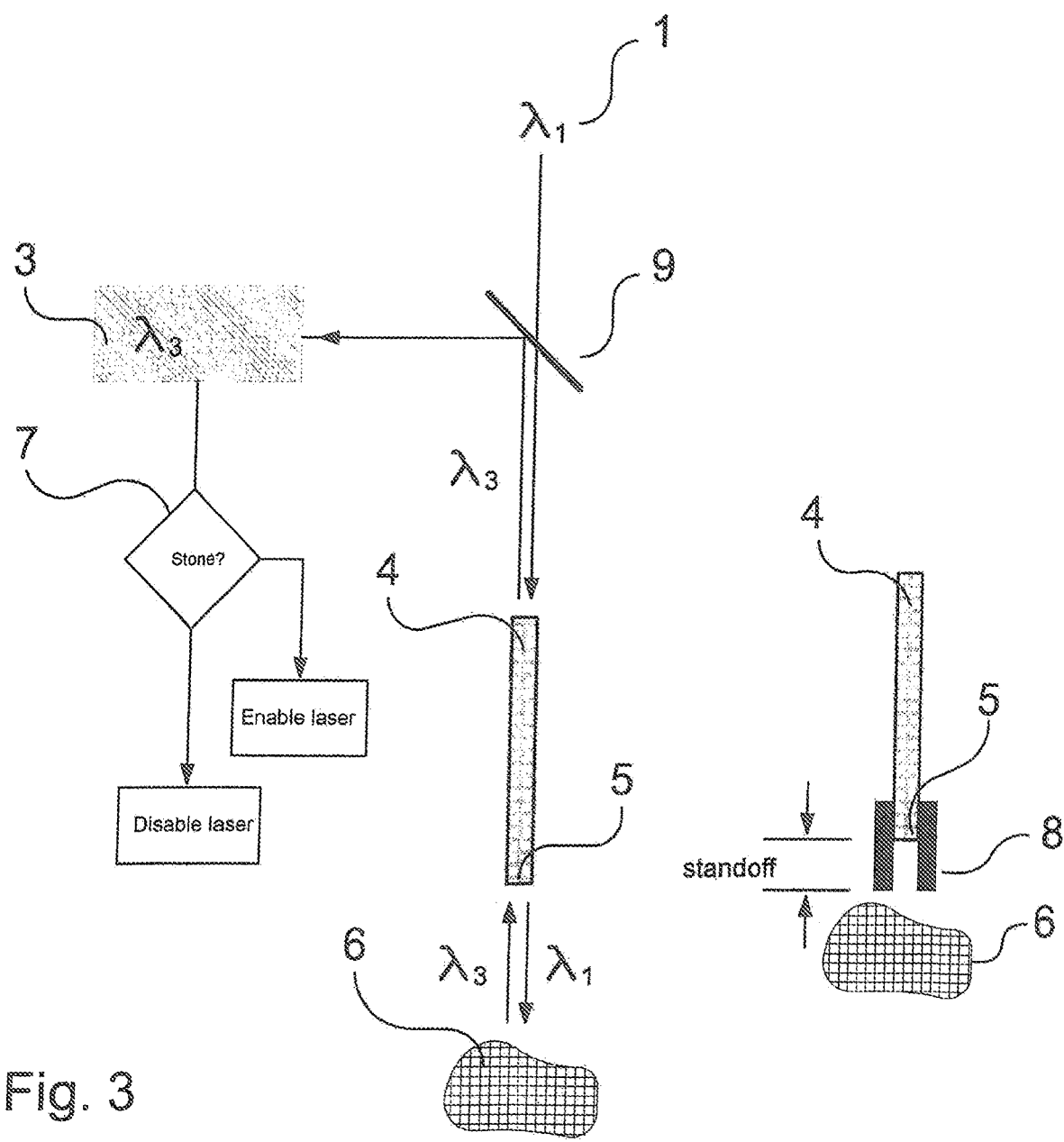
FIG. 3 is a schematic diagram of a stone detecting safety interlock arranged in accordance with the principles of a second preferred embodiment of the invention.
Figure 4:
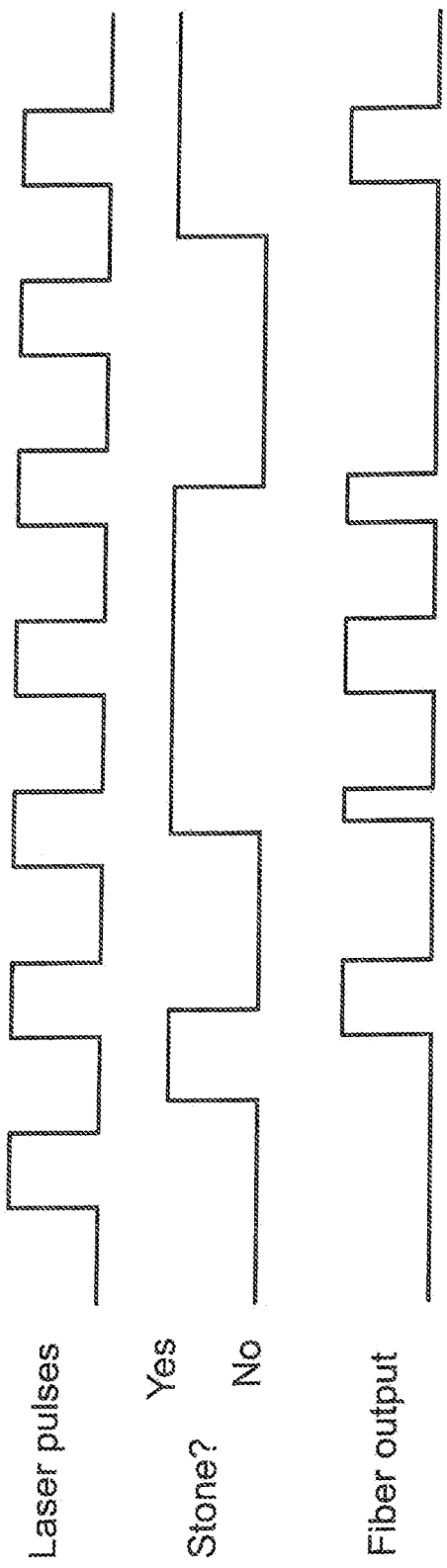
FIG. 4 is a timing diagram for the system of FIG. 3

As shown in FIGS. 3 and 4, if the system disclosed herein is used with a "SoftTip" 7 of the type described in PCT Appl. No. PCT/US2017/31091, then stone contact could be limited to lasing only when the "SoftTip" 7 is in contact with the stone 6. This would limit the effects of retro-repulsion of the stone 6.

In the system of FIG. 3, which may be applied to an optical fiber arrangement with a "SoftTip" that provides a standoff, the spectrophotometer 3 detects a wavelength(s) $\lambda 3$ resulting from reflection or emission by the stone 6 during application of the main laser wavelength $\lambda 1$. The reflected or emitted wavelength(s) $\lambda 3$ may be separated by a beam splitter 9 after traveling back through the optical fiber 4. A main laser controller, represented by decision block 7, receives a signal from the spectrophotometer that indicates whether radiation of wavelength(s) $\lambda 3$ have been detected and disables the main laser 1 if the signal has not been detected.

As shown in FIG. 4, control of the laser output may be achieved by a shutter or trigger input that only allows a pulse to be injected into the fiber when presence of the stone is indicated by a "high" or equivalent signal output by the spectrophotometer.

By only firing the laser when the fiber tip is in the optimal position for target vaporization, thereby reducing extraneous pulses that cause target retro repulsion and wear on equipment, while optimizing efficiency and reducing overall surgical time.

Finally, according to an additional optional feature of the invention, which may be applied to either embodiment, if laser 1 vaporizes a target, the resulting free floating ions and electrons produce a spectrum that can be used to identify the elemental composition of the vaporized material. The spectrometer 3 can verify this spectrum and monitor its amplitude to determine stone distance from fiber tip.

What is claimed is:

1. A system for detecting the absence of a stone during a laser lithotripsy procedure, comprising:
    a main laser for delivering laser energy having a first wavelength $\lambda 1$ through an optical fiber;
    a ferrule or sleeve fitted to an end of the fiber to serve as a standoff that physically prevents contact between an end face of the fiber and the stone;
    a detector for detecting the energy reflected or emitted by the stone when the laser energy having a first wavelength $\lambda 1$ is being delivered to the stone, wherein the energy reflected or emitted by the stone includes energy having at least one additional wavelength $\lambda 3$; and
    an alarm or safety interlock for (a) generating an alarm, or (b) cutting-off or modulating the main laser, in response to detection of an absence of said additional wavelength $\lambda 3$.

2. A system as claimed in claim 1, wherein the detector is configured to detect the absence of the stone when the reflected or emitted energy having the wavelength $\lambda 3$ is below a threshold level.

3. A system as claimed in claim 1, wherein the energy reflected or emitted by the stone passes back through the optical fiber to the detector.

4. A system as claimed in claim 3, further comprising a beam splitter for separating the energy having at least one additional wavelength $\lambda 3$ from the emitted or reflected energy passing back through the optical fiber.

5. A system as claimed in claim 1, further comprising a secondary light source for delivering light having a second wavelength $\lambda 2$ through the optical fiber to the stone.

6. A system as claimed in claim 5, wherein the secondary light source is one of a laser, LED, or endoscope light.

7. A system as claimed in claim 5, wherein the secondary light source serves as an aiming beam light source.

8. A system as claimed in claim 7, wherein the secondary light source is a pulsed UV-VIS-IR laser.

9. A system as claimed in claim 1, wherein the main laser is a pulsed laser.

10. A system as claimed in claim 9, wherein the main laser is a pulsed Holmium laser.

11. A system as claimed in claim 9, wherein the laser has an active mode that allows the laser to automatically pulse after detecting radiation reflected or emitted by the stone.

12. A system as claimed in claim 1, wherein the detector is a spectrometer, and the spectrometer is configured to analyze stone or vaporized material composition.

13. A system for detecting the absence of a stone during a laser lithotripsy procedure, comprising:
- a main laser for delivering laser energy having a first wavelength through an optical fiber;
- a detector for detecting the energy reflected or emitted by the stone when the laser energy having a first wavelength is being delivered to the stone, wherein the energy reflected or emitted by the stone passes back through the optical fiber to the detector and includes energy having at least one additional wavelength; and
- an alarm or safety interlock for cutting-off or modulating the main laser, in response to detection of an absence of said additional wavelength.

14. A system as claimed in claim 13, wherein the detector is configured to detect the absence of the stone when the reflected or emitted energy having the additional wavelength is below a threshold level.

15. A system as claimed in claim 13, further comprising a beam splitter for separating the energy having at least one additional wavelength from the emitted or reflected energy passing back through the optical fiber.

* * * * *